United States Patent
Chen et al.

(10) Patent No.: US 11,068,025 B2
(45) Date of Patent: Jul. 20, 2021

(54) SMART WEARABLE DEVICE AND CONTROL METHOD FOR SMART WEARABLE DEVICE

(71) Applicant: HUAWEI TECHNOLOGIES CO., LTD., Guangdong (CN)

(72) Inventors: Yushan Chen, Shenzhen (CN); Xueyan Huang, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 0 days.

(21) Appl. No.: 15/843,999

(22) Filed: Dec. 15, 2017

(65) Prior Publication Data
US 2018/0113486 A1 Apr. 26, 2018

Related U.S. Application Data

(63) Continuation of application No. PCT/CN2016/076053, filed on Mar. 10, 2016.

(30) Foreign Application Priority Data

Jun. 17, 2015 (CN) .......................... 201510338262.3

(51) Int. Cl.
*G06F 1/16* (2006.01)
*G06F 3/0354* (2013.01)
(Continued)

(52) U.S. Cl.
CPC ............ *G06F 1/163* (2013.01); *A61B 5/1122* (2013.01); *G06F 1/1694* (2013.01); *G06F 3/017* (2013.01);
(Continued)

(58) Field of Classification Search
CPC ............... G06F 3/0488; G06F 3/04883; G06F 3/04886; G06F 3/03547; G06F 3/017; G06F 1/163; G06F 1/1694
See application file for complete search history.

(56) References Cited

U.S. PATENT DOCUMENTS 6,619,835 B2 * 9/2003 Kita ........................ G04G 21/00
368/281
8,725,842 B1 5/2014 Al-Nasser
(Continued)

FOREIGN PATENT DOCUMENTS

CN 103150063 6/2013
CN 104090649 10/2014
(Continued)

OTHER PUBLICATIONS

Extended European Search Report, dated Mar. 7, 2018, in European Application No. 16810758.9 (7 pp.).
(Continued)

*Primary Examiner* — Kwang-Su Yang
(74) *Attorney, Agent, or Firm* — Fish & Richardson P.C.

(57) ABSTRACT

A smart wearable device and a control method for a smart wearable device relate to the field of computer devices. The method includes: detecting a first touch-control operation that is in a fixing band touch-control area, and obtaining first operation information of the first touch-control operation (101); and generating a control instruction according to the first operation information, and executing the control instruction (102). A control manner for the smart wearable device can be added by using a touch-control operation on a fixing band, operability and human-machine interactivity of the smart wearable device are improved, and disadvantages of undiversified operation manners and low interactivity that are caused when an operation is performed on
(Continued)

only a part such as a dial or by using only a part such as a crown are overcome.

4 Claims, 7 Drawing Sheets

(51) Int. Cl.
    *G06F 3/01*         (2006.01)
    *G06F 3/0488*     (2013.01)
    *A61B 5/11*       (2006.01)

(52) U.S. Cl.
    CPC ........ *G06F 3/03547* (2013.01); *G06F 3/0488* (2013.01); *G06F 3/04883* (2013.01); *G06F 3/04886* (2013.01); *A61B 2562/0219* (2013.01)

(56) References Cited

U.S. PATENT DOCUMENTS

| | | | |
|---|---|---|---|
| 9,594,427 B2 * | 3/2017 | Priyantha | ................ G06F 3/017 |
| 9,904,254 B1 * | 2/2018 | Hariri | .................... G04G 17/08 |
| 2009/0187121 A1 | 7/2009 | Evans | |
| 2010/0219943 A1 | 9/2010 | Vanska et al. | |
| 2011/0248945 A1 | 10/2011 | Higashitani | |
| 2012/0019563 A1 | 1/2012 | Misawa et al. | |
| 2013/0191773 A1 | 7/2013 | Edwards | |
| 2014/0064037 A1 | 3/2014 | Alameh et al. | |
| 2014/0104180 A1 | 4/2014 | Schaffer | |
| 2015/0111558 A1 | 4/2015 | Yang | |
| 2015/0153854 A1 | 6/2015 | Stewart et al. | |
| 2015/0227245 A1 * | 8/2015 | Inagaki | ................. G06F 3/0412 345/173 |
| 2016/0091867 A1 * | 3/2016 | Mansour | ................. G06F 1/163 368/294 |
| 2016/0203362 A1 * | 7/2016 | Huang | .................... G06F 3/017 726/19 |
| 2016/0328147 A1 * | 11/2016 | Zhang | ................... G06F 3/0482 |

FOREIGN PATENT DOCUMENTS

| | | |
|---|---|---|
| CN | 104317394 | 1/2015 |
| CN | 104461004 | 3/2015 |
| CN | 104978142 | 10/2015 |
| KR | 20110059798 A | 6/2011 |
| KR | 20110100232 A | 9/2011 |
| KR | 20150045257 A | 4/2015 |
| KR | 20150061420 A | 6/2015 |
| WO | WO2015038684 | 3/2015 |
| WO | WO2015060856 | 4/2015 |

OTHER PUBLICATIONS

International Search Report dated Jun. 13, 2016 in corresponding International Patent Application No. PCT/CN2016/076053.
Office Action issued in Korean Application No. 10-2018-7000896 dated Jun. 28, 2019, 13 pages (with English translation).
Office Action issued in Korean Application 2018-7000896 dated Dec. 12, 2019, 6 pages (with English translation).
EPO Summons to attent oral proceedings pursuant to Rule 115(1) EPC issued in European Application No. 16810758.9 dated Aug. 19, 2020, 10 pages.

* cited by examiner

Slide up and down to switch rows of keys

SMART WEARABLE DEVICE AND CONTROL METHOD FOR SMART WEARABLE DEVICE

CROSS-REFERENCE TO RELATED APPLICATIONS

This application is a continuation of International Application No. PCT/CN2016/076053, filed on Mar. 10, 2016, which claims priority to Chinese Patent Application No. 201510338262.3, filed on Jun. 17, 2015. The disclosures of the aforementioned applications are hereby incorporated by reference in their entireties.

TECHNICAL FIELD

The present disclosure relates to the field of computer devices, and in particular, to a smart wearable device and a control method for a smart wearable device.

BACKGROUND

A smart watch is an emerging smart wearable device. The smart watch runs a smart operating system, and can be connected to a network and can be used to synchronize content such as calls, SMS messages, emails, photographs, and music on a mobile phone, so that a user can use various functions on the mobile phone without needing to operate the mobile phone.

Currently, there may be the following several manners of performing an operation on a smart watch. In one manner, a crown component is retained on the smart watch, and the crown component may be turned to perform a zooming operation in an interface and choose various options. In another manner, a moving track of a user on a touchscreen of the smart watch is sensed to enter a text and choose various options.

The inventor finds that at least the following problems exist in the prior art.

Operations performed by turning the crown component are excessively undiversified, and as relatively few functions are implemented, human-machine interactivity is reduced. In addition, an area of the touchscreen of a dial of the smart watch is relatively small. Consequently, accuracy of performing an operation on the touchscreen is relatively low. In this manner, human-machine interactivity is also reduced.

SUMMARY

To resolve a prior-art problem of relatively low interactivity caused by undiversified control manners of a smart wearable device, embodiments of the present disclosure provide a smart wearable device and a control method for a smart wearable device. The technical solutions are as follows.

According to a first aspect, an embodiment of the present disclosure provides a control method of a smart wearable device, where the smart wearable device includes a fixing band, a fixing band touch-control area is set on the fixing band, and the method includes:

detecting a first touch-control operation that is in the fixing band touch-control area, and obtaining first operation information of the first touch-control operation; and generating a control instruction according to the first operation information, and executing the control instruction.

In a first possible implementation of the first aspect, the smart wearable device includes a display screen, and a display screen touch-control area is set on the display screen; and when a second touch-control operation in the display screen touch-control area is detected, the generating a control instruction according to the first operation information includes:

when the second touch-control operation in a display screen area of the smart wearable device is detected, generating the control instruction according to the first operation information and second operation information of the second touch-control operation.

With reference to the first aspect or the first possible implementation of the first aspect, in a second possible implementation of the first aspect, the first operation information includes at least one of a touch-control strength value or a deformation degree value, and the control instruction includes a control degree parameter; and the generating a control instruction according to the first operation information includes:

determining a value of the control degree parameter according to at least one of the touch-control strength value or the deformation degree value; and generating the control instruction according to the value of the control degree parameter.

With reference to the first aspect or the first possible implementation of the first aspect, in a third possible implementation of the first aspect, the control instruction includes a control degree parameter; and the generating a control instruction according to the first operation information includes:

obtaining a current acceleration value of the smart wearable device;

determining a value of the control degree parameter according to the acceleration value and the first operation information; and generating the control instruction according to the value of the control degree parameter.

With reference to the first aspect or the first possible implementation of the first aspect, in a fourth possible implementation of the first aspect, the first touch-control operation includes a sliding operation used to switch an interface, a display area is set on the fixing band, and before the detecting a first touch-control operation that is in the fixing band touch-control area, the method further includes:

displaying a first keyboard area of a virtual keyboard in the display area; and the generating a control instruction according to the first operation information, and executing the control instruction includes:

generating an interface switching instruction according to the first operation information, and executing the interface switching instruction to display a second keyboard area in the display area, where the first keyboard area and the second keyboard area are different.

With reference to any one of the first aspect to the third possible implementation of the first aspect, in a fifth possible implementation of the first aspect, the first touch-control operation includes at least one of a pulling operation, a swaying operation, or a shaking operation, where the pulling operation is an operation of pulling the fixing band in a direction parallel to an axis of the fixing band;

the swaying operation is an operation of swaying the fixing band in a direction perpendicular to a plane of the fixing band; and the shaking operation is an operation of fixing one end of the fixing band and irregularly shaking the other end of the fixing band.

With reference to any one of the first aspect to the fifth possible implementation of the first aspect, in a sixth possible implementation of the first aspect, the fixing band includes a first fixing band section and a second fixing band section, and the first operation information includes third operation information of a touch-control operation in an area of the first fixing band section and fourth operation information of a touch-control operation in an area of the second fixing band section; and correspondingly, the generating a control instruction according to the first operation information includes:

generating the control instruction according to at least one of the third operation information or the fourth operation information.

According to a second aspect, an embodiment of the present disclosure provides another smart wearable device, where the smart wearable device includes a processor and a fixing band, the fixing band includes a mechanical sensor, and a fixing band touch-control area is set on the fixing band, where the mechanical sensor is configured to: detect a first touch-control operation that is in the fixing band touch-control area, and obtain first operation information of the first touch-control operation; and the processor is configured to: generate a control instruction according to the first operation information obtained by the mechanical sensor, and execute the control instruction.

In a first possible implementation of the second aspect, the smart wearable device further includes a display screen, and a display screen touch-control area is set on the display screen; and the display screen is configured to detect a second touch-control operation that is in the display screen touch-control area; and the processor is configured to generate the control instruction according to the first operation information and the second operation information of the second touch-control operation in the display screen touch-control area.

With reference to the second aspect or the first possible implementation of the second aspect, in a second possible implementation of the second aspect, the first operation information includes at least one of a touch-control strength value or a deformation degree value, and the control instruction includes a control degree parameter;

the processor is configured to: determine a value of the control degree parameter according to at least one of the touch-control strength value or the deformation degree value, and generate the control instruction according to the value of the control degree parameter.

With reference to the second aspect or the first possible implementation of the second aspect, in a third possible implementation of the second aspect, the smart wearable device further includes an acceleration sensor, the acceleration sensor is configured to obtain a current acceleration value of the smart wearable device, and the control instruction includes a control degree parameter; and the processor is configured to: determine a value of the control degree parameter according to the acceleration value obtained by the acceleration sensor and the first operation information, and generate the control instruction according to the value of the control degree parameter.

With reference to the second aspect or the first possible implementation of the second aspect, in a fourth possible implementation of the second aspect, the first touch-control operation includes a sliding operation used to switch an interface, and a display area is set on the fixing band, and is used to display a first keyboard area of a virtual keyboard;

correspondingly, the processor is configured to generate an interface switching instruction according to the first operation information; and the display area is further configured to display a second keyboard area according to the interface switching instruction generated by the processor, where the first keyboard area and the second keyboard area are different.

With reference to any one of the second aspect to the third possible implementation of the second aspect, in a fifth possible implementation of the second aspect, the first touch-control operation includes at least one of a pulling operation, a swaying operation, or a shaking operation, where the pulling operation is an operation of pulling the fixing band in a direction parallel to an axis of the fixing band;

the swaying operation is an operation of swaying the fixing band in a direction perpendicular to a plane of the fixing band; and the shaking operation is an operation of fixing one end of the fixing band and irregularly shaking the other end of the fixing band.

With reference to any one of the second aspect to the fifth possible implementation of the second aspect, in a sixth possible implementation of the second aspect, the fixing band includes a first fixing band section and a second fixing band section, and the first operation information includes third operation information of a touch-control operation in an area of the first fixing band section and fourth operation information of a touch-control operation in an area of the second fixing band section; and correspondingly, the processor is configured to generate the control instruction according to at least one of the third operation information or the fourth operation information.

A first touch-control operation that is performed by a user on a fixing band is detected on a smart wearable device, first operation information of the first touch-control operation is obtained, and a control instruction is generated according to the first operation information and the control instruction is executed. A control manner for the smart wearable device can be added by using a touch-control operation on the fixing band, operability and human-machine interactivity of the smart wearable device are improved, and disadvantages of undiversified operation manners and low interactivity that are caused when an operation is performed on only a part such as a dial or by using only a part such as a crown are overcome.

BRIEF DESCRIPTION OF DRAWINGS

To describe the technical solutions in the embodiments of the present disclosure more clearly, the following briefly describes the accompanying drawings for describing the embodiments. Apparently, the accompanying drawings in the following description show merely some embodiments of the present disclosure, and a person of ordinary skill in the art may still derive other drawings from these accompanying drawings without creative efforts.

DESCRIPTION OF EMBODIMENTS

To make the objectives, technical solutions, and advantages of the present disclosure clearer, the following further describes the embodiments of the present disclosure in detail with reference to the accompanying drawings.

Embodiment 1

Figure 1:
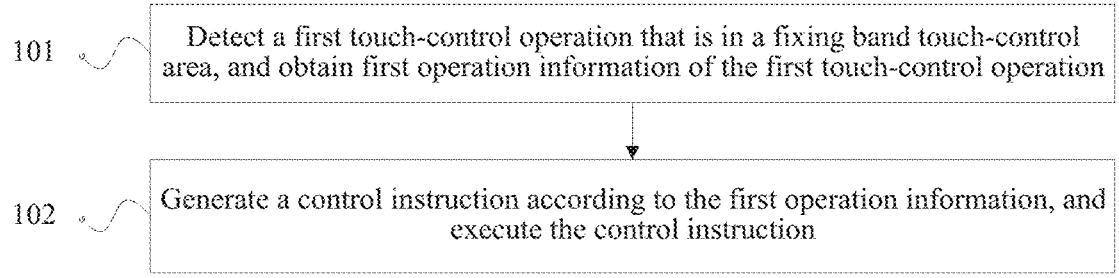
FIG. 1 is a flowchart of a control method for a smart wearable device according to Embodiment 1 of the present disclosure.

This embodiment of the present disclosure provides a control method for a smart wearable device, as shown in FIG. 1. This method embodiment is applied to a smart wearable device with a fixing band in which a mechanical sensor is disposed. The smart wearable device includes the fixing band. A fixing band touch-control area is set on the fixing band.

The method includes the following steps.

101. Detect a first touch-control operation that is in the fixing band touch-control area, and obtain first operation information of the first touch-control operation.

102. Generate a control instruction according to the first operation information, and execute the control instruction.

A control instruction corresponding to the first operation information is obtained from a correspondence between operation information and a control instruction according to the first operation information, and the control instruction is executed.

The fixing band is equipment used to fix the smart wearable device to the body of a user or to a fixture. When the smart wearable device is a smart watch, the fixing band may be a watch band.

The mechanical sensor disposed in the fixing band includes one or more of a deformation sensitive sensor, a pressure sensitive sensor, or a tension sensitive sensor. External forces of different types such as a tapping operation, a sliding operation, a pulling operation, a twisting operation, a swaying operation, a shaking operation, and a pressing operation that are applied by the user to the fixing band may be detected by using the deformation sensitive sensor, the pressure sensitive sensor, and the tension sensitive sensor. For the deformation sensitive sensor, a positive direction and a negative direction of the fixing band may be preset. Correspondingly, a positive-direction deformation and a negative-direction deformation may be sensed. The positive direction and the negative direction are merely relative concepts that are set for ease of distinguishing.

The pulling operation is an operation of pulling the fixing band in a direction parallel to an axis of the fixing band.

The swaying operation is an operation of swaying the fixing band in a direction perpendicular to a plane of the fixing band.

The shaking operation is an operation of fixing one end of the fixing band and irregularly shaking the other end of the fixing band.

Further, the fixing band may include a first fixing band section and a second fixing band section. The two fixing band sections may allow the user to separately operate one section or combinatively operate the two sections. When the smart wearable device is vertically worn, the first fixing band section and the second fixing band section may be respectively an upper fixing band section and a lower fixing band section. The upper fixing band section and the lower fixing band section are merely relative concepts that are set for distinguishing. When the smart wearable device is horizontally placed, the first fixing band section may be a half section on a left side of the smart wearable device, and the second fixing band section may be a half section on a right side of the smart wearable device.

The user may perform a touch-control operation on either half section of the fixing band, obtain operation information corresponding to the touch-control operation, and eventually generate a control instruction according to the operation information. The user may also separately perform touch-control operations on the two fixing band sections of the fixing band, and obtain operation information corresponding to a touch-control operation on each fixing band section; or obtain a touch-control operation on each fixing band section, and determine a corresponding control instruction according to operation information of the two touch-control operations. Same or different touch-control operations may be performed on the two fixing band sections. Multiple sensing areas may further be preset on the fixing band, and a corresponding identifier may be defined for each sensing area, to determine a touch position of the user on the fixing band.

The first operation information in step 102 may include an external force type, an external force position, and an external force direction of the first touch-control operation. Correspondingly, the correspondence between the operation information and the control instruction may be a correspondence between an external force type, an external force position, and an external force direction and a control instruction, as shown in the following Table 1.

TABLE 1

| External force type | External force position | External force direction | Control instruction |
|---|---|---|---|
| Tap | The first fixing band section or the second fixing band section | / | Trigger an action that includes, but is not limited to: acceleration of a race car in a racing game; braking of a race car in a racing game; use of a weapon in an action-adventure game; and focusing or triggering of photographing in a photographing scenario |
| Slide | The first fixing band section or the second fixing band section | Upward in a length direction of the band | An object on a screen moves in a particular direction, where a moving speed of the object corresponds to a moving speed of a touch point on the band, including, but not limited to: forward movement of a race car in a racing game in a direction away from the screen |
| Slide | The first fixing band section and the second fixing band section | A touch point on the first fixing band section moves upward/downward in the length direction of the band, and a touch point on the second fixing band section moves downward/upward in the length direction of the band | Zoom in/out content displayed on a display screen; and Adjust (increase/decrease) a focal distance in a photographing scenario, where an adjustment degree corresponds to a moving distance of a touch point |
| Slide | The first fixing band section | Upward in the length direction of the fixing band/Leftward in a direction perpendicular to the length direction of the fixing band on the band | Move backward to select a start point in a text selection scenario, where a backward-movement degree corresponds to a moving distance |
| Slide | The second fixing band section | Downward in the length direction of the fixing band/Rightward in a direction perpendicular to the length direction of the fixing band on the band | Move forward to select an end point in a text selection scenario, where a forward-movement degree corresponds to a moving distance |
| Slide | The first fixing band section and the second fixing band section | Upward in the length direction of the fixing band/Leftward in a direction perpendicular to the length direction of the fixing band on the band, and downward in the length direction of the fixing band/Rightward in a direction perpendicular to the length direction of the fixing band on the band | Move backward to select a start point and move forward to select an end point in a text selection scenario, where a backward-movement/forward-movement degree corresponds to a moving distance; zooming in/out of content displayed on a screen and expand/reduce a range of selected content on a screen |
| Slide | The first fixing band section and the second fixing band section | Upward/downward in the length direction of the fixing band on the fixing band/in a direction perpendicular to the length direction of the fixing band on the fixing band | Adjust a position of displayed content on the band. For example, in a photographing scenario, move upward/downward in the length direction of the band on the band to adjust a display position of a previewed image on the band; and in an input scenario, move upward/downward in a direction perpendicular to the length direction of the band on the band to switch a virtual keyboard |
| Pull | The first fixing band section or the second fixing band section | Pull in the length direction of the fixing band | Pull an item in a gaming scenario, where a pulling degree corresponds to a strength of pulling the band |
| Sway | The first fixing band section or the second fixing band section | Sway up and down in a direction perpendicular to a plane of the fixing band | An item or a character in a gaming scenario is bounced off or falls, where a bouncing or falling distance corresponds to a distance of swaying the band |

TABLE 1-continued

| External force type | External force position | External force direction | Control instruction |
|---|---|---|---|
| Shake | The first fixing band section or the second fixing band section | One end of the band is approximately still, and the other end irregularly moves at random positions | A hook or a fish in a fishing game moves as the band shakes, where magnitude of movement corresponds to magnitude of shaking |

In addition, because use manners vary among applications, the applications may set the correspondence between operation information and the control instruction according to requirements of the applications. Correspondingly, step 102 may be:

obtaining a program identifier of an application program currently running on the smart wearable device, and obtaining, according to the program identifier, a correspondence that is between operation information and a control instruction and that corresponds to the application program; and obtaining, according to the first operation information, a control instruction corresponding to the first operation information from the correspondence that is between the operation information and the control instruction and that corresponds to the application program, and executing the control instruction.

The program identifier of the application program may be a name, an installation time, an installation position, or the like of the application program.

In this embodiment of the present disclosure, a first touch-control operation that is performed by a user in a fixing band touch-control area is detected on a smart wearable device, first operation information of the first touch-control operation is obtained, and a control instruction is generated according to the first operation information and the control instruction is executed. A control manner for the smart wearable device can be added by using a touch-control operation on a fixing band, operability and human-machine interactivity of the smart wearable device are improved, and disadvantages of undiversified operation manners and low interactivity that are caused when an operation is performed on only a part such as a dial or by using only a part such as a crown are overcome.

Embodiment 2

Figure 2:
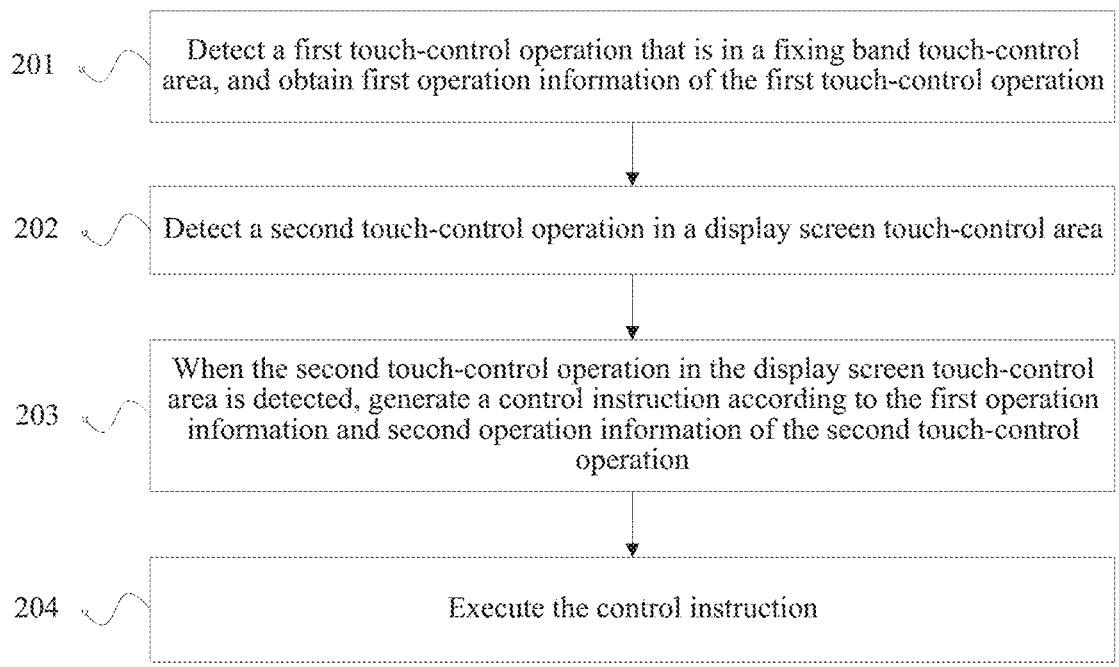
FIG. 2 is a flowchart of a control method for a smart wearable device according to Embodiment 2 of the present disclosure.

This embodiment of the present disclosure provides a control method for a smart wearable device, as shown in FIG. 2. This method embodiment is applied to a smart wearable device with a fixing band in which a mechanical sensor is disposed. The smart wearable device includes the fixing band. A fixing band touch-control area is set on the fixing band. The smart wearable device further includes a display screen. A display screen touch-control area is set on the display screen.

The method includes the following steps.

201. Detect a first touch-control operation that is in the fixing band touch-control area, and obtain first operation information of the first touch-control operation.

In this embodiment of the present disclosure, after a user performs a second touch-control operation on the display screen of the smart wearable device, in combination with the first touch-control operation that is performed by the user in the fixing band touch-control area, the first operation information of the first touch-control operation and second operation information of the second touch-control operation are used together to determine an eventual control instruction.

Both the first touch-control operation and the second touch-control operation may include, but are not limited to, a tapping operation, a long-pressing operation, and a sliding operation.

202. Detect a second touch-control operation in the display screen touch-control area.

203. When the second touch-control operation in the display screen touch-control area is detected, generate a control instruction according to the first operation information and second operation information of the second touch-control operation.

A control instruction corresponding to the first operation information and the second operation information is obtained from a correspondence among first operation information, second operation information, and a control instruction according to the first operation information and the second operation information.

Because use manners vary among applications, the applications may set the correspondence among the first operation information, the second operation information, and the control instruction according to requirements of the applications. Correspondingly, step 203 may be:

obtaining a program identifier of an application program currently running in the display screen touch-control area, and obtaining, according to the program identifier, a correspondence that is among first operation information, second operation information, and a control instruction and that corresponds to the application program; and obtaining, according to the first operation information and the second operation information, a control instruction corresponding to the first operation information and the second operation information from the correspondence that is among the first operation information, the second operation information, and the control instruction and that corresponds to the application program.

A photographing scenario is used as an example for description. An example in which the smart wearable device is a smart watch is used. The user presses and holds a display screen of the smart watch by using a finger. At this time, the smart watch senses that a long-pressing event, that is, a second touch-control operation, is triggered. At the same time, the user performs, on a fixing band, a touch-control operation, that is, a first touch-control operation, of sliding in a length direction of the fixing band or in a direction perpendicular to the length direction of the watch band by using another finger.

A control instruction generated according to first operation information of the first touch-control operation and second operation information of the second touch-control operation is an instruction of controlling content displayed on the display screen of the smart watch to be zoomed in or zoomed out.

204. Execute the control instruction.

In this embodiment of the present disclosure, a first touch-control operation that is performed by a user in a fixing band touch-control area is detected on a smart wearable device, first operation information of the first touch-control operation is obtained, and a control instruction is generated according to the first operation information and the control instruction is executed. A control manner for the smart wearable device can be added by using a touch-control operation on a fixing band, operability and human-machine interactivity of the smart wearable device are improved, and disadvantages of undiversified operation manners and low interactivity that are caused when an operation is performed on only a part such as a dial or by using only a part such as a crown are overcome.

Embodiment 3

Figure 3:
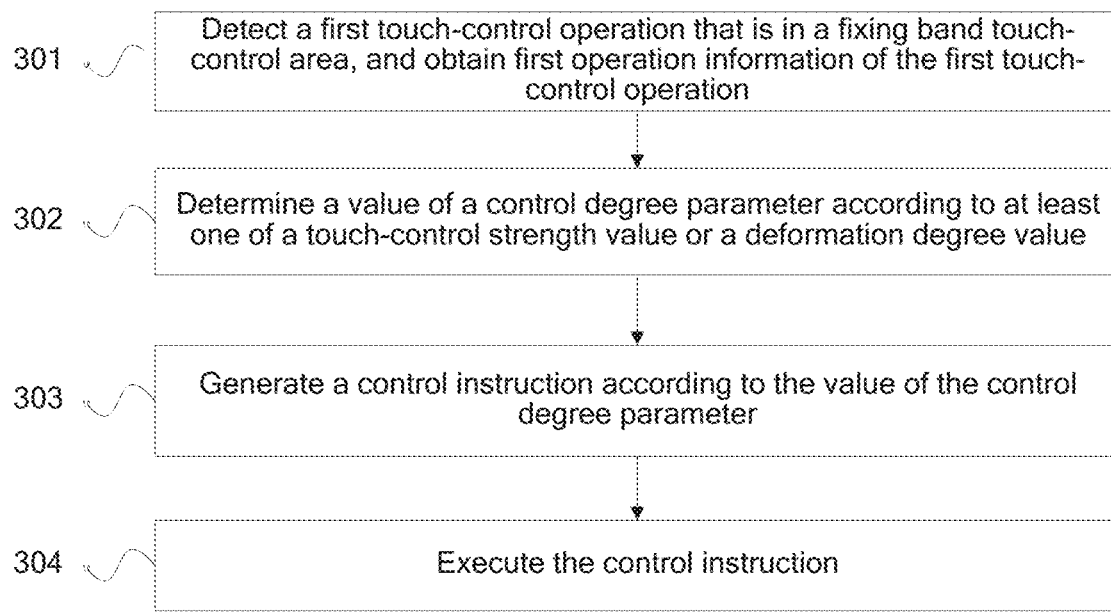
FIG. 3 is a flowchart of a control method for a smart wearable device according to Embodiment 3 of the present disclosure.

This embodiment of the present disclosure provides a control method for a smart wearable device, as shown in FIG. 3. This method embodiment is applied to a smart wearable device with a fixing band in which a mechanical sensor is disposed.

The method includes the following steps.

301. Detect a first touch-control operation that is in a fixing band touch-control area, and obtain first operation information of the first touch-control operation.

The first operation information includes at least one of a touch-control strength value or a deformation degree value.

Correspondingly, the first operation information may be at least one of a touch-control strength value that is sensed by using a pressure sensitive sensor in the fixing band or a deformation degree value that is sensed by using a deformation sensitive sensor in the fixing band.

302. Determine a value of a control degree parameter according to at least one of a touch-control strength value or a deformation degree value.

The value of the control degree parameter is obtained from a correspondence between a touch-control strength value and a value of the control degree parameter according to the touch-control strength value; or the value of the control degree parameter is obtained from a correspondence between a deformation degree value and a value of the control degree parameter according to the deformation degree value; or the value of the control degree parameter is obtained from a correspondence among a touch-control strength value, a deformation degree value, and a value of the control degree parameter according to the touch-control strength value and the deformation degree value.

303. Generate a control instruction according to the value of the control degree parameter.

The control instruction includes the control degree parameter. By using different control degree parameters, different control effects can be achieved by applying different strengths to perform a same touch-control operation.

For example, the first touch-control operation is a sliding operation on the fixing band. If a touch-control strength value is larger, a gaming movement of a corresponding operation in a game running on the smart wearable device is bigger. This may be that a control instruction corresponding to the sliding operation is an operation of controlling a steering wheel to steer in a racing game. When a touch-control strength value is larger, a corresponding turning angle is larger.

For another example, a current control instruction is sliding a picture on a screen of the smart wearable device. A sliding speed may be controlled according to the touch-control strength value or the deformation degree value. When a touch-control strength value or deformation degree value is larger, a sliding speed is higher. When a touch-control strength value or deformation degree value is smaller, a sliding speed is lower.

Therefore, the control instruction may be generated by using the following step:

obtaining, according to the value of the control degree parameter, a control instruction corresponding to the value of the control degree parameter from a correspondence between a value of the control degree parameter and a control instruction.

304. Execute the control instruction.

In this embodiment of the present disclosure, a first touch-control operation that is performed by a user in a fixing band touch-control area is detected on a smart wearable device, first operation information of the first touch-control operation is obtained, and a control instruction is generated according to the first operation information and the control instruction is executed. A control manner for the smart wearable device can be added by using a touch-control operation on a fixing band, operability and human-machine interactivity of the smart wearable device are improved, and disadvantages of undiversified operation manners and low interactivity that are caused when an operation is performed on only a part such as a dial or by using only a part such as a crown are overcome.

Embodiment 4

Figure 4:
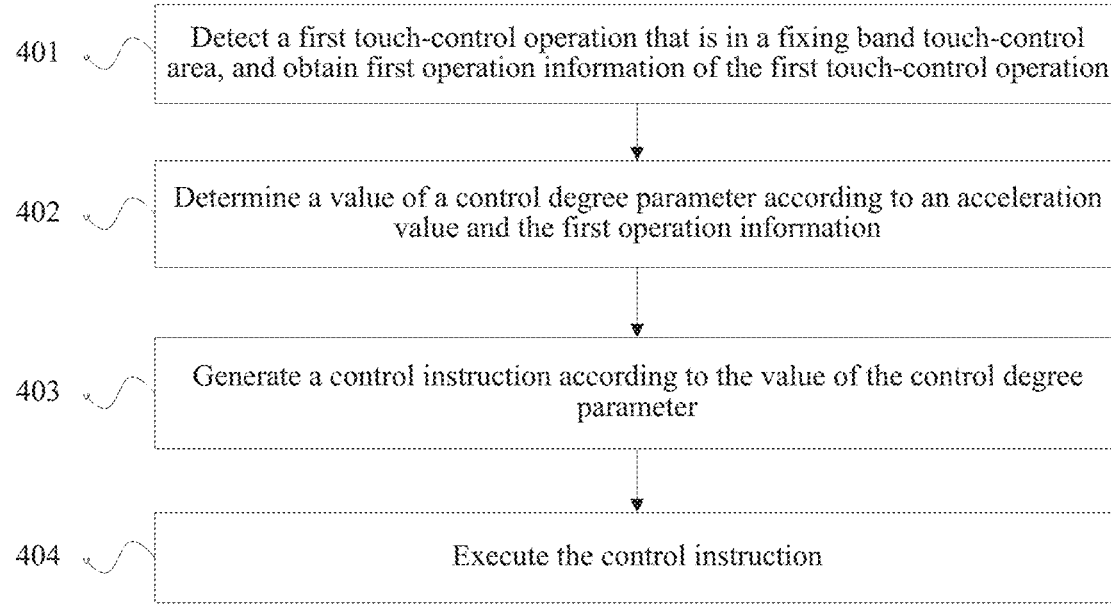
FIG. 4 is a flowchart of a control method for a smart wearable device according to Embodiment 4 of the present disclosure.

This embodiment of the present disclosure provides a control method for a smart wearable device, as shown in FIG. 4. This method embodiment is applied to a smart wearable device with a fixing band in which a mechanical sensor is disposed.

The method includes the following steps.

401. Detect a first touch-control operation that is in a fixing band touch-control area, and obtain first operation information of the first touch-control operation.

In this embodiment of the present disclosure, the smart wearable device may further include a triaxial acceleration sensor. A value of an acceleration corresponding to each of three axes of the smart wearable device may be sensed by using the acceleration sensor.

The sensed values of the accelerations corresponding to the axes may further be combined with a touch-control operation performed by a user on the fixing band to control a strength of executing a control instruction.

An implementation scenario in this case may be: the user performs an operation of a motion sensing game in a motion sensing game application, and a more realistic motion effect can be achieved through movement by controlling the smart wearable device. For example, the user sways the smart wearable device up and down to play a trampoline game. Similarly, hurdling, skiing, surfing, and other games may also be played.

402. Determine a value of a control degree parameter according to an acceleration value and the first operation information.

The value of the control degree parameter is obtained from a correspondence among an acceleration value, operation information, and a value of the control degree parameter according to the acceleration value and the first operation information.

403. Generate a control instruction according to the value of the control degree parameter.

A control instruction corresponding to the value of the control degree parameter is obtained from a correspondence between a value of the control degree parameter and a control instruction according to the control degree parameter.

404. Execute the control instruction.

For example, when playing a trampoline game, the user sways the smart wearable device up and down. In this case, the smart wearable device senses an acceleration parameter of swaying up or down, a deformation sensitive sensor senses a deformation of the fixing band, and a control instruction is eventually obtained by using the deformation and a position and a direction of the deformation. The control instruction may be motion control or jump control in the trampoline game. Correspondingly, a strength of executing the motion control or the jump control in the control instruction may be controlled according to the acceleration parameter. When the acceleration parameter is larger, a corresponding motion magnitude or jump magnitude is larger. When the acceleration parameter is smaller, a corresponding motion magnitude or jump magnitude is smaller.

In this embodiment of the present disclosure, a first touch-control operation that is performed by a user in a fixing band touch-control area is detected on a smart wearable device, first operation information of the first touch-control operation is obtained, and a control instruction is generated according to the first operation information and the control instruction is executed. A control manner for the smart wearable device can be added by using a touch-control operation on a fixing band, operability and human-machine interactivity of the smart wearable device are improved, and disadvantages of undiversified operation manners and low interactivity that are caused when an operation is performed on only a part such as a dial or by using only a part such as a crown are overcome.

Embodiment 5

Figure 5:
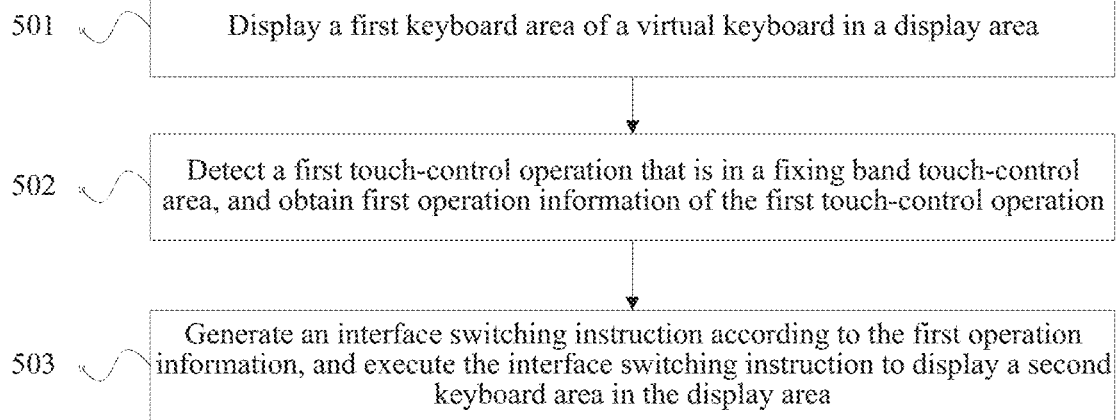
FIG. 5 is a flowchart of a control method for a smart wearable device according to Embodiment 5 of the present disclosure.

This embodiment of the present disclosure provides a control method for a smart wearable device, as shown in FIG. 5. This method embodiment is applied to a smart wearable device with a fixing band in which a mechanical sensor is disposed. In this embodiment of the present disclosure, a display area may further be included in the fixing band, and may be used to display a virtual keyboard for entering a text.

The method includes the following steps.

501. Display a first keyboard area of the virtual keyboard in the display area.

Correspondingly, the virtual keyboard further includes a second keyboard area. The first keyboard area and the second keyboard area are different.

Because an area of the display area is relatively small, all keys cannot be displayed. Correspondingly, multiple keyboard areas may be included in the virtual keyboard, and different keys are included in different keyboard areas. An interface switching instruction may be determined by using a touch-control operation on the fixing band, to switch the keyboard areas. For example, keys displayed in the first keyboard area are ASDFG, and keys displayed in the second keyboard area are ZXCVB. The first keyboard area and the second keyboard area are merely used to distinguish different keyboard areas, and do not limit a quantity of keyboard areas, and all keyboard areas may include all keys in a keyboard.

502. Detect a first touch-control operation that is in a fixing band touch-control area, and obtain first operation information of the first touch-control operation.

The first touch-control operation may be a tapping operation, a long-pressing operation, or a sliding operation.

503. Generate an interface switching instruction according to the first operation information, and execute the interface switching instruction to display a second keyboard area in the display area.

Figure 6:
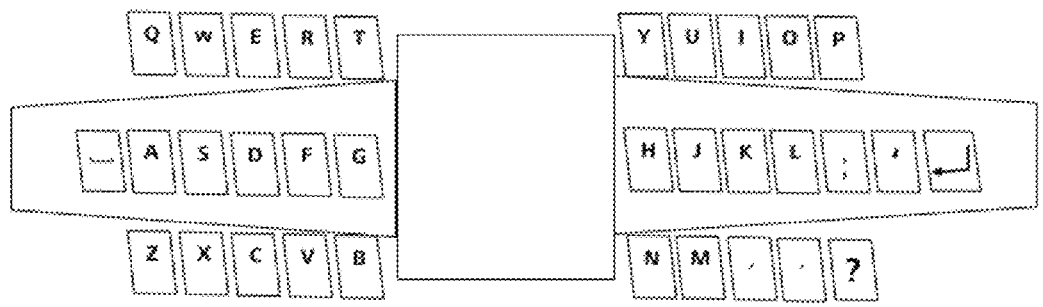
FIG. 6 is a schematic operational diagram in the control method for a smart wearable device according to Embodiment 5 of the present disclosure.

A text input scenario is used as an example for description. An example in which the smart wearable device is a smart watch is used. A display area is further set in a watch band of the smart watch. A user may horizontally place the smart watch in front. The smart watch displays a character in the display area on the watch band. When a touch-control operation of sliding is performed, a corresponding control instruction is switching different rows of keys. When a touch-control operation of tapping is performed, a corresponding control instruction is entering a character. In this case, specific entered character content is determined according to a preset area tapped by the user in the watch band and a correspondence between an area and a character. A schematic operational diagram of this example is shown in FIG. 6.

In this embodiment of the present disclosure, a first touch-control operation that is performed by a user in a fixing band touch-control area is detected on a smart wearable device, first operation information of the first touch-control operation is obtained, and a control instruction is generated according to the first operation information and the control instruction is executed. A control manner for the smart wearable device can be added by using a touch-control operation on a fixing band, operability and human-machine interactivity of the smart wearable device are improved, and disadvantages of undiversified operation manners and low interactivity that are caused when an operation is performed on only a part such as a dial or by using only a part such as a crown are overcome.

Embodiment 6

Figure 7:
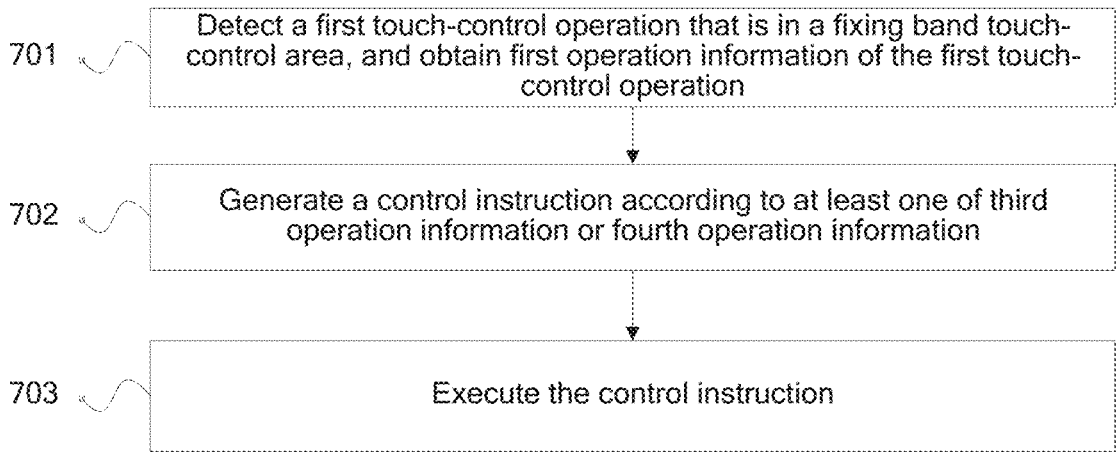
FIG. 7 is a flowchart of a control method for a smart wearable device according to Embodiment 6 of the present disclosure.

This embodiment of the present disclosure provides a control method for a smart wearable device, as shown in FIG. 7. This method embodiment is applied to a smart wearable device with a fixing band in which a mechanical sensor is disposed.

The method includes the following steps.

701. Detect a first touch-control operation that is in a fixing band touch-control area, and obtain first operation information of the first touch-control operation.

In this embodiment of the present disclosure, the fixing band includes a first fixing band section and a second fixing band section. The first operation information includes third operation information of a touch-control operation in an area of the first fixing band section and fourth operation information of a touch-control operation in an area of the second fixing band section.

702. Generate a control instruction according to at least one of third operation information or fourth operation information.

A control instruction corresponding to the third operation information is obtained from a correspondence between operation information and a control instruction according to the third operation information; or a control instruction corresponding to the fourth operation information is obtained from a correspondence between operation information and a control instruction according to the fourth operation information; or a control instruction corresponding to the third operation information and the fourth operation information is obtained from a correspondence among third operation information, fourth operation information, and a control instruction according to the third operation information and the fourth operation information.

Because use manners vary among applications, the applications may set the correspondence among the third operation information, the fourth operation information, and the control instruction according to requirements of the applications. Correspondingly, step 702 may be:

obtaining a program identifier of an application program currently running in a display screen touch-control area, and obtaining, according to the program identifier, a correspondence that is among third operation information, fourth operation information, and a control instruction and that corresponds to the application program; and obtaining, according to the third operation information and the fourth operation information, a control instruction corresponding to the third operation information and the fourth operation information from the correspondence that is among the third operation information, the fourth operation information, and the control instruction and that corresponds to the application program.

703. Execute the control instruction.

The control method for a smart wearable device in this embodiment of the present disclosure is described below by using several specific implementation scenarios as examples.

Figure 8:
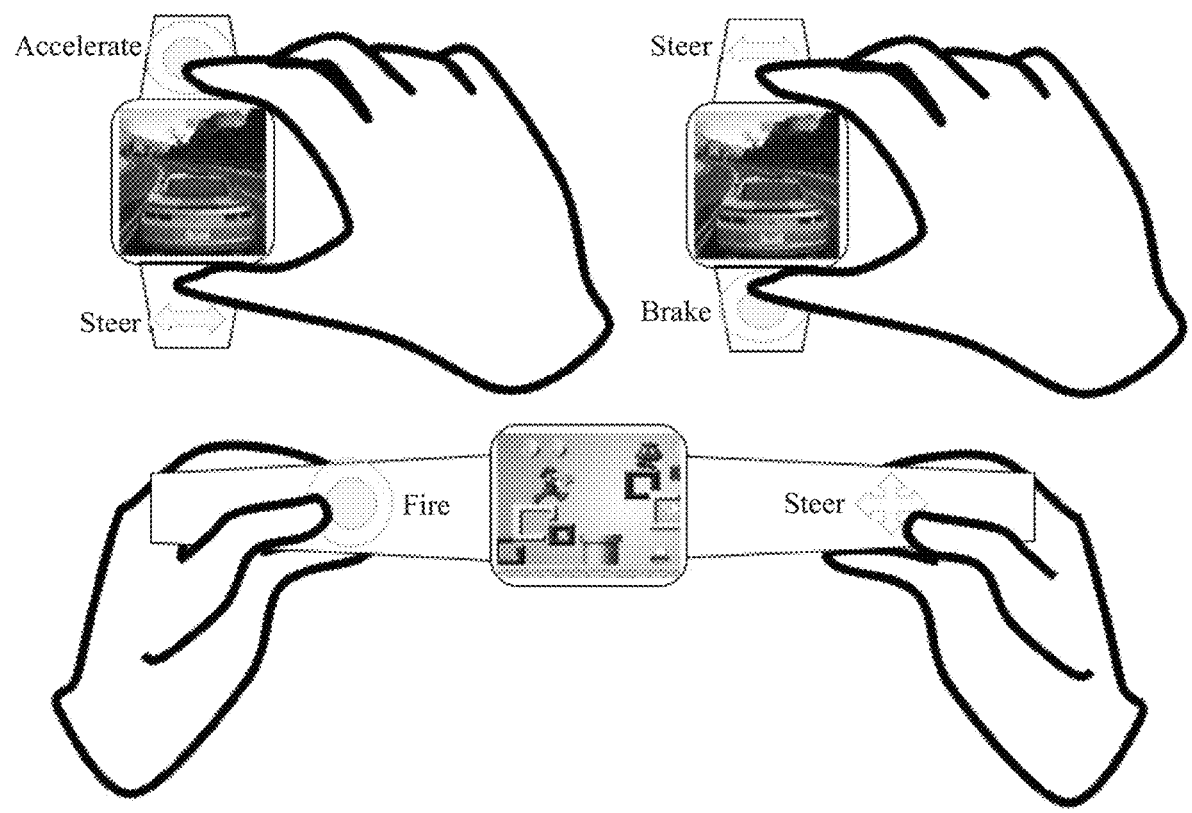
FIG. 8 is a schematic operational diagram in the control method for a smart wearable device according to Embodiment 6 of the present disclosure.

A gaming scenario is used as an example for description. An example in which the smart wearable device is a smart watch is used. The smart watch is currently in a vertically held state, and a user runs a racing game application on the smart wearable device. The user may perform a touch-control operation of tapping on an upper fixing band section by using a finger, and a corresponding control instruction is accelerating a race car; and perform, on a lower fixing band section by using another finger, a touch-control operation of sliding in a length direction of the fixing band or in a direction perpendicular to the length direction of the fixing band, and a corresponding control instruction is controlling a traveling direction of the race car. A control manner may also be that the user performs, on the upper fixing band section by using a finger, a touch-control operation of sliding in the length direction of the fixing band or in the direction perpendicular to the length direction of the fixing band, and a corresponding control instruction is controlling the traveling direction of the race car; and performs a touch-control operation of tapping on the lower fixing band section by using another finger, and a corresponding control instruction is controlling the race car to brake. In an action-adventure game application, the smart watch may also be horizontally held. In this case, the user may perform a touch-control operation of tapping on the upper fixing band section by using a finger, and a corresponding control instruction is using a weapon to perform an attack operation; and perform, on the lower fixing band section by using another finger, a touch-control operation of sliding in the length direction of the fixing band or in the direction perpendicular to the length direction of the fixing band, and a corresponding control instruction is controlling a traveling direction of a character. A schematic operational diagram of this example is shown in FIG. 8.

Figure 9:
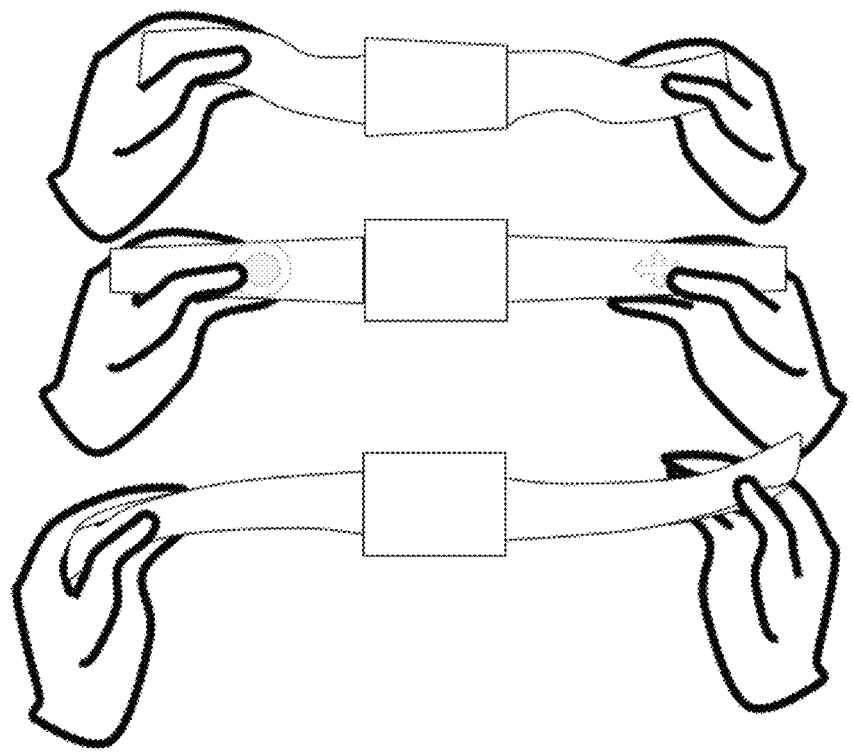
FIG. 9 is a schematic operational diagram in the control method for a smart wearable device according to Embodiment 6 of the present disclosure.

In addition, when the smart watch is in a horizontally held state, a deformation of the fixing band may also be caused by performing a touch-control operation of twisting or swaying on two fixing band sections by the user, and a corresponding control instruction is an action corresponding to the deformation. A schematic operational diagram of this example is shown in FIG. 9.

Figure 10:
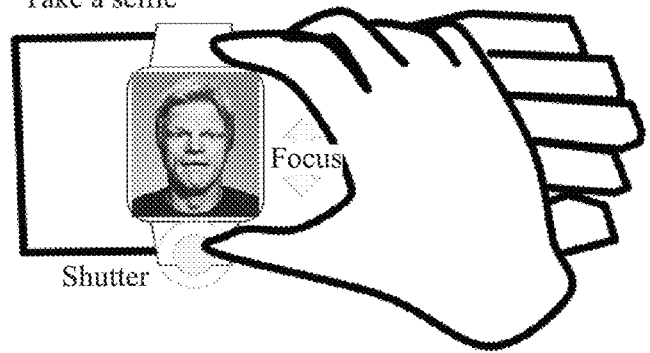
FIG. 10 is a schematic operational diagram in the control method for a smart wearable device according to Embodiment 6 of the present disclosure.

A photographing scenario is used as an example for description. An example in which the smart wearable device is a smart watch is used. When the smart watch is used for photographing or used as a remote control to control a device such as a mobile phone or a tablet computer of the user to take a photograph, the user may perform a touch-control operation of sliding in the length direction of the fixing band on the fixing band by using two fingers at the same time, and a corresponding control instruction is focusing. For example, the user slides an index finger upward/downward on the upper fixing band section, and at the same time slides a thumb downward/upward on the lower fixing band section. The user may also perform a touch-control operation of sliding two fingers at the same time along a circumference of a wrist away from/toward a dial, and a corresponding control instruction is making a lens zoom in/out. After a focal distance is adjusted and the lens is set, a touch-control operation of tapping in a preset area of the fixing band is then performed, and a corresponding control instruction is focusing or triggering photographing. A schematic operational diagram of this example is shown in FIG. 10. In addition, the foregoing manner used for focusing may also be used to zoom in or zoom out content displayed on a screen.

Figure 11:
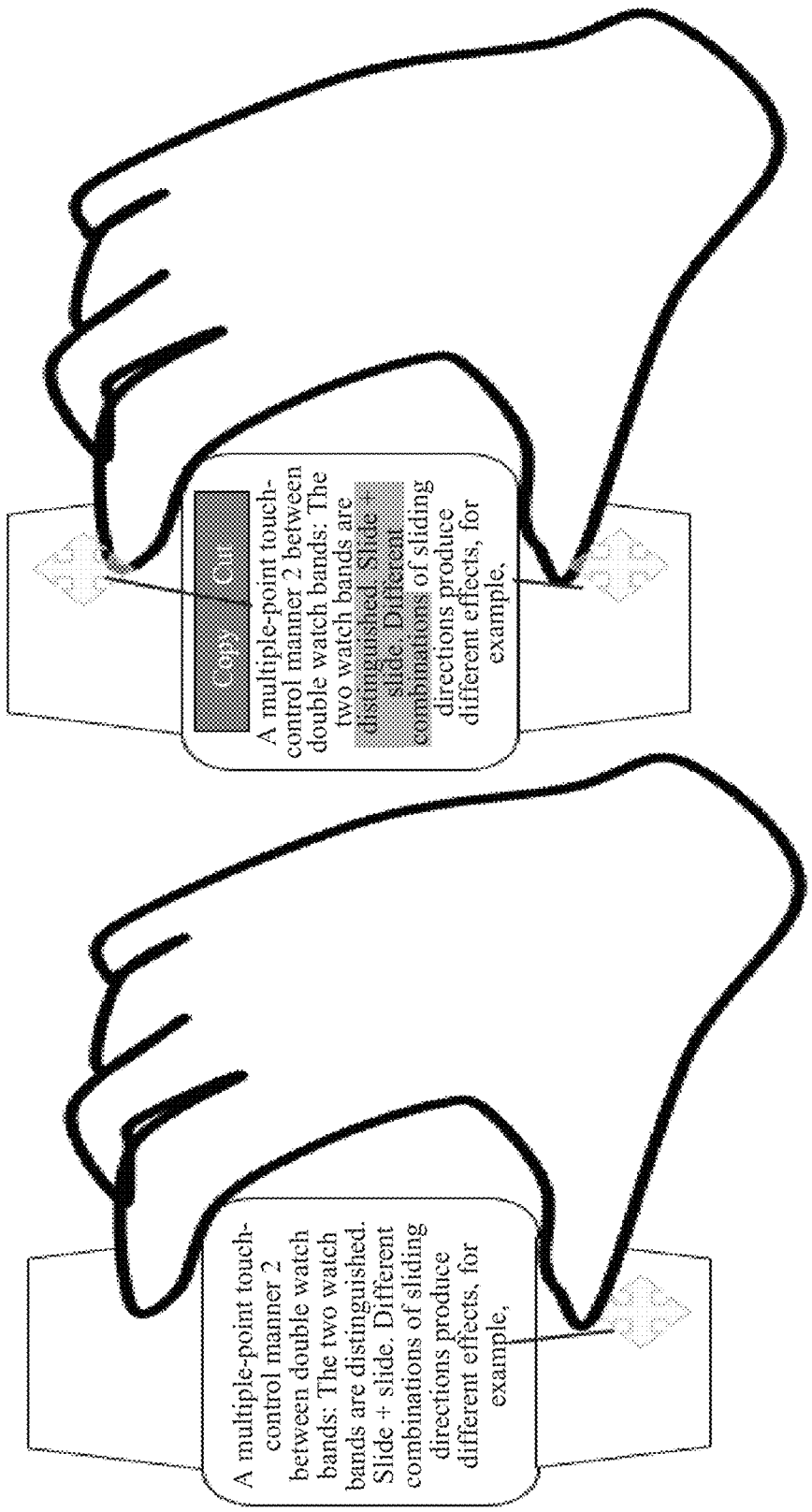
FIG. 11 is a schematic operational diagram in the control method for a smart wearable device according to Embodiment 6 of the present disclosure.

A content selection scenario is used as an example for description. An example in which the smart wearable device is a smart watch is used. The user may perform a touch-control operation of long-pressing or perform a touch-control operation of sliding on the fixing band, and a corresponding control instruction is controlling movement of a cursor on a display screen; and may also perform a touch-control operation of sliding in different directions on the fixing band, and a corresponding control instruction is selecting a content range. Text content is used as an example. The user slides upward or leftward on the upper fixing band section to move a start point of a selected text backward to extend a range of selection and slides downward or rightward on the lower fixing band section to move an end point of the selected text forward to extend a range of selection, alternatively, the user slides upward or leftward on the lower fixing band section to move a start point of a selected text backward to extend a range of selection and slides downward or rightward on the upper fixing band section to move an end point of the selected text forward to extend a range of selection. A schematic operational diagram of this example is shown in FIG. 11.

The upper fixing band section and the lower fixing band section in this embodiment of the present disclosure may be a first fixing band section and a second fixing band section.

In this embodiment of the present disclosure, a first touch-control operation that is performed by a user in a fixing band touch-control area is detected on a smart wearable device, first operation information of the first touch-control operation is obtained, and a control instruction is generated according to the first operation information and the control instruction is executed. A control manner for the smart wearable device can be added by using a touch-control operation on a fixing band, operability and human-machine interactivity of the smart wearable device are improved, and disadvantages of undiversified operation manners and low interactivity that are caused when an operation is performed on only a part such as a dial or by using only a part such as a crown are overcome.

Embodiment 7

Figure 12:
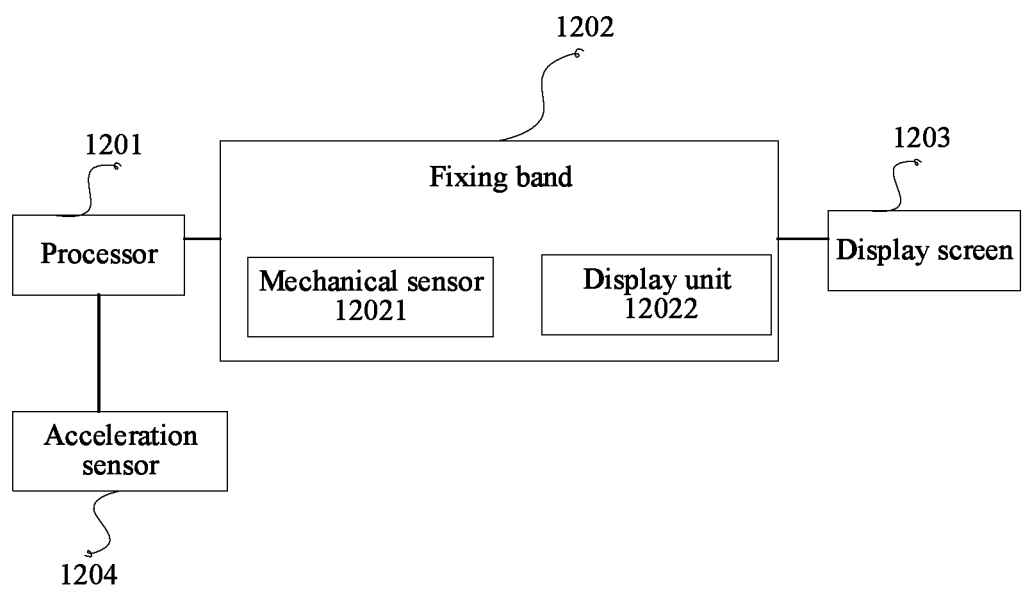
FIG. 12 is a schematic structural diagram of a smart wearable device according to Embodiment 7 of the present disclosure.

This embodiment of the present disclosure provides a control apparatus of a smart wearable device. The control apparatus of a smart wearable device is applied to a smart wearable device with a fixing band in which a mechanical sensor is disposed, as shown in FIG. 12. The apparatus includes:

a processor 1201 and a fixing band 1202, where the fixing band 1202 includes a mechanical sensor 12021, and a fixing band touch-control area is set on the fixing band.

The mechanical sensor 12021 is configured to: detect a first touch-control operation that is in the fixing band touch-control area, and obtain first operation information of the first touch-control operation.

The processor 1201 is configured to: generate a control instruction according to the first operation information obtained by the mechanical sensor 12021, and execute the control instruction.

The processor 1201 is connected to a memory, and is configured to read code stored in the memory.

The smart wearable device further includes a display screen 1203, and a display screen touch-control area is set on the display screen.

The display screen 1203 is configured to: detect a second touch-control operation that is in the display screen touch-control area, and obtain second operation information of the second touch-control operation.

The processor 1201 is configured to generate the control instruction according to the first operation information and the second operation information of the second touch-control operation in the display screen touch-control area.

The first operation information includes at least one of a touch-control strength value or a deformation degree value, and the control instruction includes a control degree parameter.

The processor 1201 is configured to: determine a value of the control degree parameter according to at least one of the touch-control strength value or the deformation degree value, and generate the control instruction according to the value of the control degree parameter.

The smart wearable device further includes an acceleration sensor 1204. The acceleration sensor 1204 is configured to obtain a current acceleration value of the smart wearable device. The control instruction includes a control degree parameter.

The processor 1201 is configured to: determine a value of the control degree parameter according to the acceleration value obtained by the acceleration sensor and the first operation information, and generate the control instruction according to the value of the control degree parameter.

The first touch-control operation includes a sliding operation used to switch an interface. A display area 12022 is set on the fixing band 1202, and is used to display a first keyboard area of a virtual keyboard.

Correspondingly, the processor 1201 is configured to generate an interface switching instruction according to the first operation information.

The display area 12022 is further configured to display a second keyboard area according to the interface switching instruction generated by the processor 1201, where the first keyboard area and the second keyboard area are different.

The first touch-control operation includes a pulling operation, a swaying operation, and a shaking operation.

The pulling operation is an operation of pulling the fixing band 1202 in a direction parallel to an axis of the fixing band 1202.

The swaying operation is an operation of swaying the fixing band 1202 in a direction perpendicular to a plane of the fixing band 1202.

The shaking operation is an operation of fixing one end of the fixing band 1202 and irregularly shaking the other end of the fixing band 1202.

The fixing band 1202 includes a first fixing band section and a second fixing band section, and the first operation information includes third operation information of a touch-control operation in an area of the first fixing band section and fourth operation information of a touch-control operation in an area of the second fixing band section.

Correspondingly, the processor 1201 is configured to generate the control instruction according to at least one of the third operation information or the fourth operation information.

In this embodiment of the present disclosure, a first touch-control operation that is performed by a user in a fixing band touch-control area is detected on a smart wearable device, first operation information of the first touch-control operation is obtained, and a control instruction is generated according to the first operation information and the control instruction is executed. A control manner for the smart wearable device can be added by using a touch-control operation on a fixing band, operability and human-machine interactivity of the smart wearable device are improved, and disadvantages of undiversified operation manners and low interactivity that are caused when an operation is performed on only a part such as a dial or by using only a part such as a crown are overcome.

A person of ordinary skill in the art may understand that all or some of the steps of the embodiments may be implemented by hardware or a program instructing related hardware. The program may be stored in a computer-readable storage medium. The storage medium may include: a read-only memory, a magnetic disk, or an optical disc.

The foregoing descriptions are merely exemplary embodiments of the present disclosure, but are not intended to limit the present disclosure. Any modification, equivalent replacement, and improvement made without departing from the spirit and principle of the present disclosure shall fall within the protection scope of the present disclosure.

What is claimed is:

1. A smart wearable device, comprising:
   a fixing band, the fixing band comprising:
      a mechanical sensor; and
      a fixing band touch-control area set on the fixing band, wherein the mechanical sensor is configured to:
         detect a first touch-control operation that is in the fixing band touch-control area, and obtain first operation information of the first touch-control operation, wherein the first touch-control operation in the fixing band touch-control area is a sliding operation, and wherein the sliding operation corresponds to a control instruction associated with a method of controlling of a currently running application;
   a display screen, the display screen comprising a display screen touch-control area set on the display screen, wherein the display screen is configured to:
      detect a second touch-control operation that is in the display screen touch-control area; and at least one processor, the at least one processor configured to:

in response to detecting both the first touch-control operation and the second touch-control operation at the same time, generate the control instruction according to a combination of the first operation information obtained by the mechanical sensor detected from the fixing band touch-control area and second operation information of the second touch-control operation in the display screen touch-control area; and execute the control instruction.

2. The smart wearable device according to claim 1, wherein the first touch-control operation comprises the sliding operation in the fixing band touch-control area in a length direction of the fixing band or in a direction perpendicular to the length direction of the fixing band, and wherein the second touch-control operation comprises a press-and-hold operation in the display screen touch-control area.

3. A control method for a smart wearable device, wherein the smart wearable device comprises a fixing band and a display screen, wherein a fixing band touch-control area is set on the fixing band, and wherein a display screen touch-control area is set on the display screen, the control method comprising:

detecting a second touch-control operation in the display screen touch-control area to obtain second operation information of the second touch-control operation;

while detecting the second touch-control operation in the display screen touch-control area, detecting a first touch-control operation in the fixing band touch-control area to obtain first operation information of the first touch-control operation, wherein the first touch-control operation in the fixing band touch-control area is a sliding operation, and wherein the sliding operation corresponds to a control instruction associated with a method of controlling of a currently running application;

generating the control instruction according to a combination of the first operation information of the first touch-control operation detected from the fixing band touch-control area and the second operation information of the second touch-control operation detected from the display screen; and executing the control instruction.

4. The method according to claim 3, wherein the first touch-control operation comprises the sliding operation in the fixing band touch-control area in a length direction of the fixing band or in a direction perpendicular to the length direction of the fixing band, and wherein the second touch-control operation comprises a press-and-hold operation in the display screen touch-control area.

* * * * *